(12) United States Patent
Budz et al.

(10) Patent No.: US 6,429,884 B1
(45) Date of Patent: Aug. 6, 2002

(54) METHOD AND APPARATUS FOR PROCESSING AND PLAYBACK OF DIGITAL IMAGES AT A DISPLAY MONITOR

(75) Inventors: Sebastian Budz, Erlangen; Klaus Ludwig, Nuremberg, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/435,441

(22) Filed: Nov. 22, 1999

(30) Foreign Application Priority Data

Nov. 24, 1998 (DE) .......................... 198 54 131

(51) Int. Cl.$^7$ .......................... G06F 3/14; G06T 17/40; A61B 6/03
(52) U.S. Cl. .................. 345/848; 345/852; 345/424; 345/419; 345/624; 600/425
(58) Field of Search ................ 345/848, 852, 345/849, 419, 427, 420, 424, 421, 623, 624, 620; 600/407, 410, 416, 417, 425

(56) References Cited

U.S. PATENT DOCUMENTS

| | | | | |
|---|---|---|---|---|
| 4,879,668 A | * | 11/1989 | Cline et al. ................. | 345/424 |
| 5,170,347 A | * | 12/1992 | Tuy et al. .................... | 345/419 |
| 5,201,035 A | * | 4/1993 | Stytz et al. ............. | 345/424 X |
| 5,371,778 A | * | 12/1994 | Yanof et al. ............ | 345/427 X |
| 5,454,371 A | * | 10/1995 | Fenster et al. .......... | 345/419 X |
| 5,623,586 A | | 4/1997 | Höhne .......................... | 345/424 |
| 5,734,384 A | * | 3/1998 | Yanof et al. ................ | 345/424 |
| 6,211,884 B1 | * | 4/2001 | Knittel et al. ............... | 345/424 |

OTHER PUBLICATIONS

"Back–to–Front Display of Voxel–Based Objects," Frieder et al., IEEE CG&A, 1985, pp. 52–60.

"Bildgebende Systeme für die medizinische Diagnostik, " Morneburg, Ed. (1995), pp. 649–651.

* cited by examiner

Primary Examiner—Raymond J. Bayerl
(74) Attorney, Agent, or Firm—Schiff Hardin & Waite

(57) ABSTRACT

In a method and apparatus for presenting and processing an image reproducible at a display monitor, wherein digital image data of an examination volume of a subject are registered with an image pickup system, such as a medical examination installation, the examination volume or a part thereof is played back at the display monitor as a three-dimensional image, and a volume region of the image is defined with a marker, this volume region or the image environment thereof being removed from the image and no longer displayed in a subsequent image presentation.

17 Claims, 3 Drawing Sheets

METHOD AND APPARATUS FOR PROCESSING AND PLAYBACK OF DIGITAL IMAGES AT A DISPLAY MONITOR

BACKGROUND OF THE INVENTION

1. Field of the Invention

The present invention is directed to a method and apparatus for the presentation and processing of an image reproducible at a display monitor, of the type wherein digital image data of an examination volume of a subject are registered with an image pick-up system such as a medical examination installation, and wherein the examination volume or a part thereof is played back as a three-dimensional image at the display monitor.

2. Description of the Prior Art

Particularly in medical technology, specific areas of the human body, for example the head, are often examined, and a specific examination volume of the patient is registered during the course of this examination, i.e. corresponding digital image data in the form of a dataset describing the entire examination volume are registered for this specific examination volume, for example a slice from the head area. The image pickup can ensue, for example, using a computed tomography apparatus, a magnetic resonance system, an X-ray examination system or, on the other hand, with an ultrasound examination system. For evaluation by the physician, the image of the examination volume that is obtained can then be output at a display monitor as volume image in the form of a projection image or a surface image or as a tomogram. On the basis of this image, the physician then makes a diagnosis. Difficulties, however, occur when a specific region of interest within the three-dimensionally displayed image is covered by a body part located in front of it. When, for example, the aorta proceeding along the spinal column is to be examined. The spinal column lying in front of the aorta (as viewed from the back of the patient) can be disturbing, i.e. the aorta itself cannot be viewed.

German OS 41 17 117 discloses an apparatus for three-dimensional presentation of spatial structures which causes parts wherein only straight section edges are achieved to be removed from a dataset according to a method that is referred to as clip lanes.

SUMMARY OF THE INVENTION

An object of the present invention is to provide a method that makes it possible to obtain a presentation of a freely selectable region of interest of the examination volume in a simple way.

This object is inventively achieved in a method wherein an examination volume of a subject is registered in the form of a set of digital image data, and wherein the image is varied in terms of its image orientation, such as by rotation, wherein a planar contour is identified in the two-dimensional image with a marker, wherein a volume region of the image is defined with the planar contour (outline) as a base area and with a direction through the overall image that is defined with respect to the image, wherein the defined volume region or the image environment thereof is removed from the image, and wherein the image is displayed without the defined volume region or the image environment thereof.

The inventive method offers the possibility of clipping or punching an arbitrary part out of the displayed image, so that this image region is no longer contained in a subsequent image presentation. The possibility is thus available of cutting out precisely those disturbing regions from the image, or the image dataset, of the examination volume that impede the view of a body section of interest. This volume regiori is defined with the marker, with the appertaining image dataset of the marked volume region being determined and this image dataset being removed from the overall image dataset of the examination volume. In a simple way, the physician can thus "tailor" an image having relevance for the diagnosis, i.e. he or she can arbitrarily modify the original image of the examination volume until a presentation which is of use to the physician has been found. It has thereby proven especially expedient when the image is variable in terms of its image orientation, particularly rotatable, i.e. the physician can arbitrarily shift or turn the displayed examination volume, or the examination volume that has already been processed, and the physician thus can set the respective image orientation or image view at which a defined image region is cut out. Inventively, the defined volume region thus always can be placed through the image with a defined direction with respect to the image independently of the of the image orientation, i.e. the marked region is always placed into the image volume with a constant direction. for example always perpendicular to the display plane. Using a track ball for image variation, for example, the physician thus rotates the image into a desired position, determines the volume region that, for example, extends perpendicularly into the presentation plane, punches this out (deletes it) and subsequently again turns the processed image somewhat in order to punch out another region whose direction into the volume proceeds somewhat differently than in the case of the first region determination, due to the rotation, and but which remains as a constant directional determination of the volume region.

In order to be able to make a pre-selection as to the presentation of the image to be processed proceeding from the registered, overall examination volume, the examination volume can be inventively displayed in a first overall image parallel to the image to be processed, whereby the image within the overall image is defined with a further marker. The registered overall image is presented on the display monitor, i.e. the overall examination volume that is displayable on the basis of the registered digital image dataset. A portion can then be selected within this overall image using a further marker, this portion then being displayed as a three-dimensional image of the examination volume. The physician can thus already make a pre-selection, i.e. he or she already effectively cuts, punches out (of the overall examination volume) a region that is of interest to the physician and is to be further-processed. A second overall image whose image plane resides perpendicularly on that of the first overall image thus can be inventively displayed parallel to the first overall image, with a further marker with which the image is defined also being allocated to the second overall image. Three images thus are displayed in parallel, two thereof serving the purpose of preprocessing, namely for the selection of an image volume region to be processed that has already been demarcated, and the other, image, which presents the volume region, then being actually processed. Volume images in the form of projection images or surface images or tomograms can be displayed as image to be processed or as the overall image.

Inventively, lines mixable into the image or into the overall images can be employed as markers, these being movable with a control unit, such as a mouse. The line mixable into the image can thereby be arbitrarily drawn with the control mouse, i.e. a cursor displayable at the monitor that draws a line can, for example, be moved with the control mouse, so that the volume region is thereby defined. This line can also be automatically closed in order to define the demarcated region. In the case of the overall images, the mixable lines can inventively represent a rectangle whose shape and/or size can be varied with the control unit. The processed image can be stored a separate image dataset, so that there is the possibility of re-displaying the already processed image for a second examination.

The object is also achieved in an apparatus for the implementation of the described method. This apparatus includes an image processor in which the digital image data of an examination volume of a subject are stored, and also has a display monitor for the playback of a three-dimensional image of the examination volume or a part thereof, with a marker for defining a volume region of the image, wherein the image processor is fashioned for generating a subsequently reproducible image in which the image dataset belonging to the defined volume region or the remaining image dataset of the image environment is no longer presented.

Inventively, the image itself can be variable in its image orientation, particularly being rotatable, using a control unit, for example a track ball.

By means of the image processor, further, the examination volume can be presented in a first, and possibly also in a second, overall image that can be reproduced parallel to the image. Moreover, a further marker can be provided for defining the image within the overall image or images. The marker can be lines mixable into the image or into the overall images that are fashioned movable or variable with a control unit. Further, a memory can be provided for storing the processed image as a separate image dataset that, just as the overall images, can be a volume image in the form of a projection image or a surface image or a tomogram.

DESCRIPTION OF THE PREFERRED EMBODIMENTS

Figure 1:
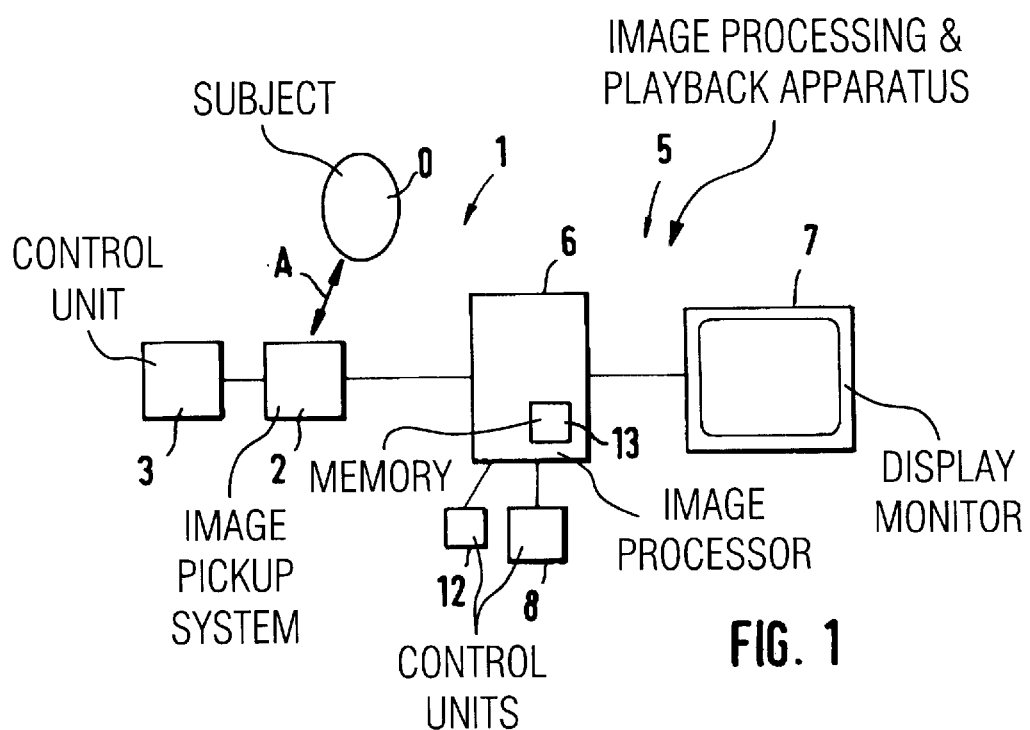
FIG. 1 is a schematic diagram of an inventive medical examination installation including an inventive apparatus for the implementation of the method.

In a schematic diagram, FIG. 1 shows a medical examination installation 1 having an image pickup system 2 that is controlled by a control unit 3. This schematic illustration shows only the relevant components; of course a medical examination installation also contains a number of other components that are of no significance here. The image pickup system 2 can, for example, be an X-ray system or an ultrasound system or a magnetic resonance system or a computed tomography system.

The digital image data of a subject O that can be determined with the image pickup system 2, (the subject O—as indicated by the double arrow A—being examined) are forwarded to an apparatus for processing and playback of registered images 5, which includes an image processor 6 as well as a display monitor 7. The images can be output at the display monitor 7. Further, a control unit 8 in the form of a control mouse, with which markings displayable at the display monitor 7 are movable, as well as a control unit 12, for example in the form of a track ball, are allocated to the image processor 6, as discussed below.

Figure 2:
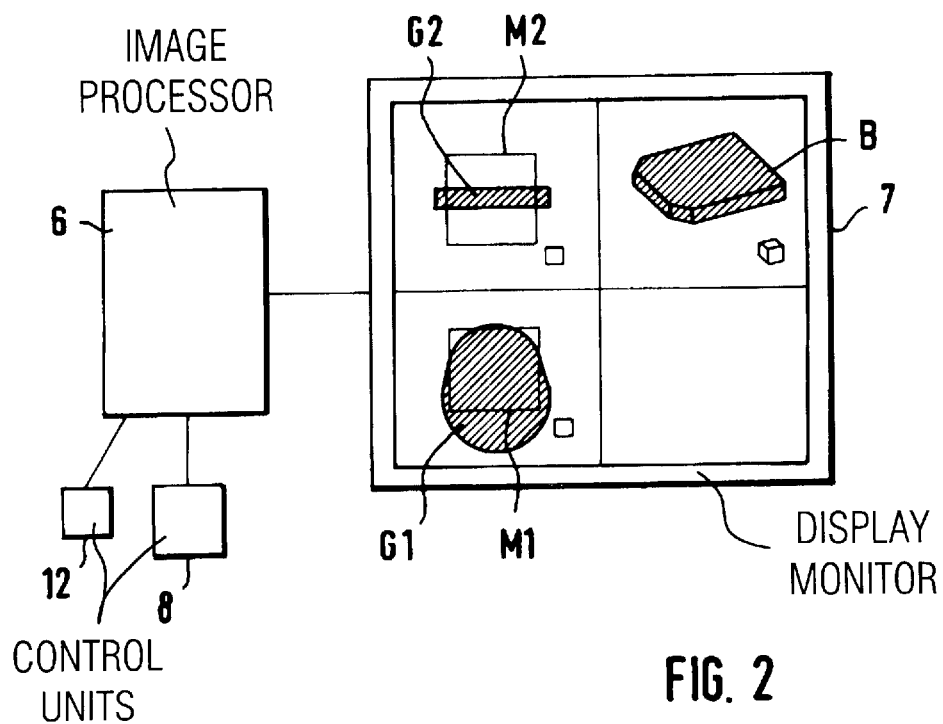
FIG. 2 is a schematic diagram of the inventive apparatus with an enlarged illustration of a presentation on the display monitor.
Figure 3:
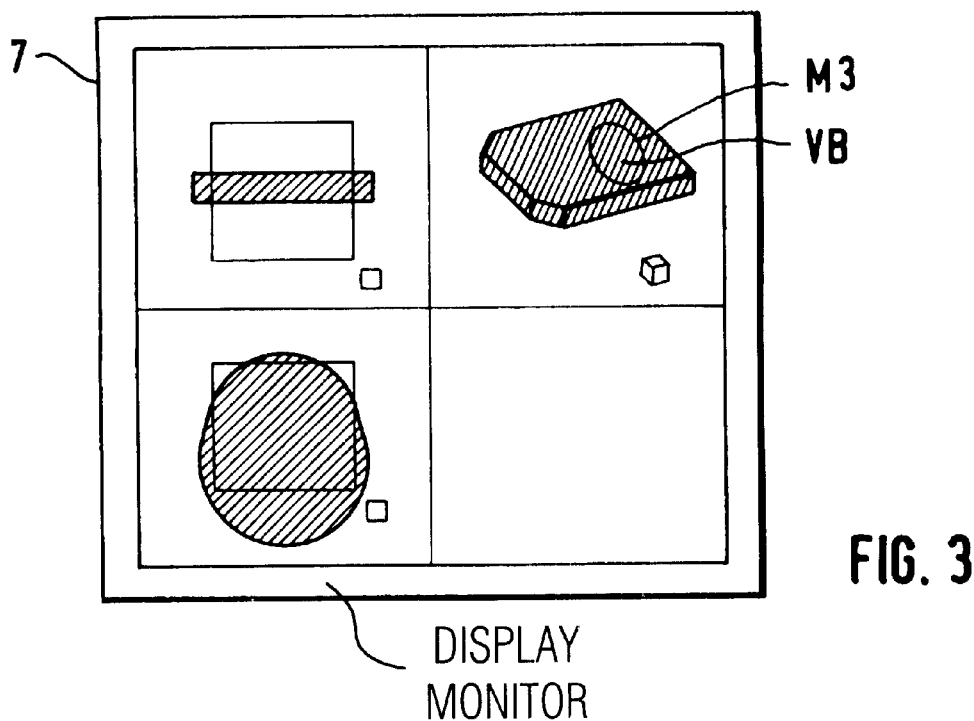
FIGS. 3–7 respectively show presentations reproduced at the display monitor.

FIG. 2 shows an example of the image presentation and image processing. Only the apparatus 5 is shown. Two overall images G1 and G2 are shown at the display monitor 7, these representing the examination volume of the subject O registered with the image pickup system 2. This can be, for example, a slice from the head of a patient, with a view onto the slice from below toward the head being shown in the overall image G1, and a view onto the slice shown in G1 from the front is shown in image G2. Marker M1, M2 each in the form of a line forming a rectangle are superimposed on the respective images G1, G2. A region of interest, namely the region located inside the rectangle, can be clipped from the overall image presentation with these markers M1, M2. The respective markers M1, M2 are variable with the control means 8, i.e. they can be displaced and varied in shaped and/or size. As a result, it is possible for the physician to cut out a volume region of interest from the registered overall image, or from the registered, overall examination volume, this then being displayed in the image B. The region of the examination volume shown therein corresponds to the region that is located inside the markers M1, M2 residing perpendicularly to one another. The region of interest is thus cut out from the overall image dataset of the registered examination volume with the markers M1, M2, this image dataset then being shown in the form of the image B. This can then be further-processed by the physician, as shown in FIGS. 3 through 7.

Figure 4:
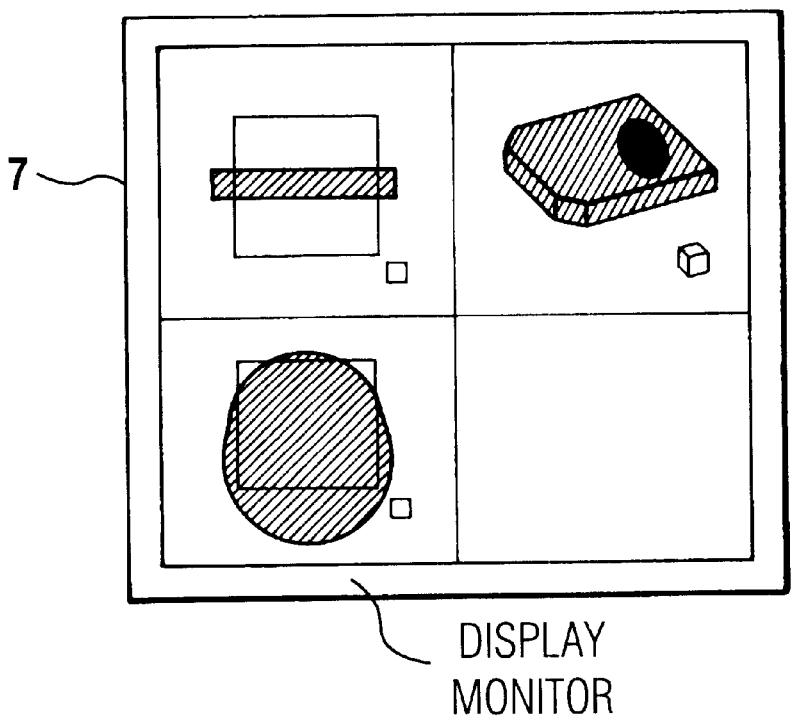

FIGS. 3 through 7 show only the image presentations reproduced on the display monitor 7. These are respective projection images wherein structures are three-dimensionally presented, i.e. or e can effectively look through the displayed volume and view body parts located in the volume, with parts lying farther toward the back being covered by parts lying in front of them. In order to eliminate such image portions that disturb the view onto body parts actually of interest, for example a specific bone, a vessel or the like—see FIG. 3—, a third marker M3 in the form of a closed line is mixed in on the image B when the user gives a corresponding command, a volume region extending into the plane of presentation being defined with this marker M3. The marker M3 can be moved with the control unit 8 or can be drawn with a cursor. The image processor 6 then determines the digital image dataset belonging to this defined volume region VB, i.e. this region is defined in terms of image data. As FIG. 4 shows, this volume region VB can now be removed, can be cut out, from the image B; the image dataset of the image B is reduced by the image dataset of the volume region VB. An image region, for example a bone or the like, that impedes the view onto a body part of interest is thus cut out of the displayed view.

Figure 5:
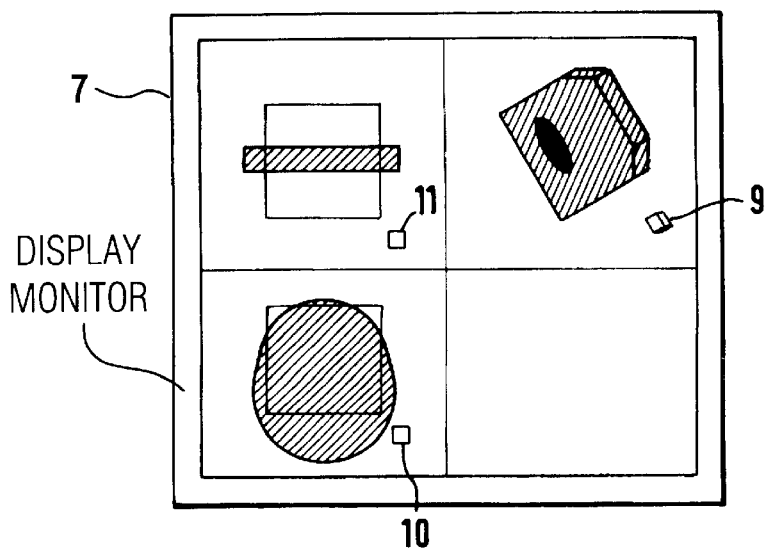
Figure 6:
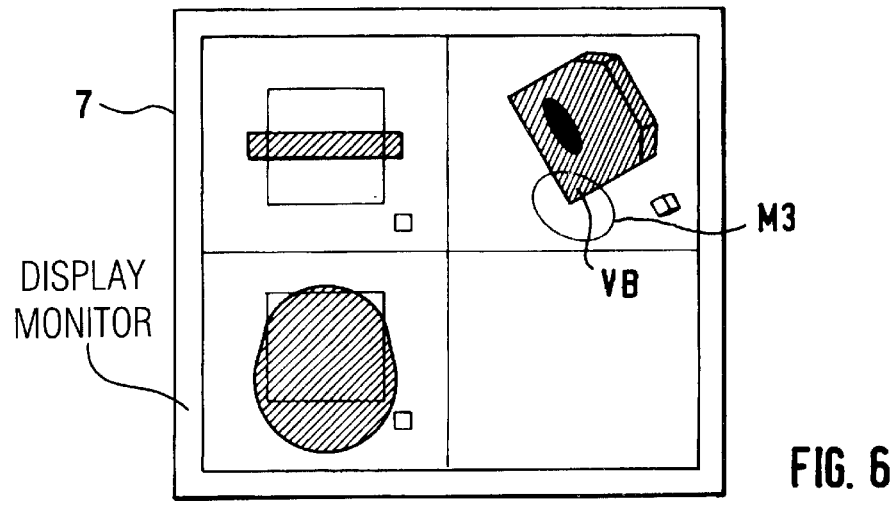
Figure 7:
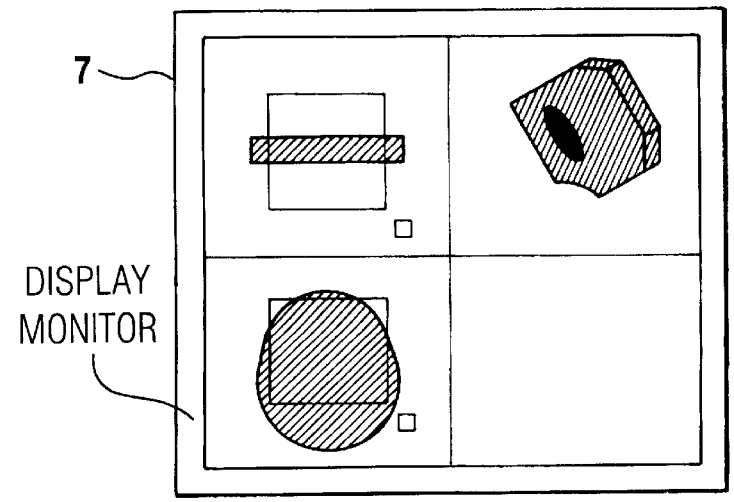

A shown in FIG. 5, the physician can likewise rotate the image orientation of the image B via a suitable control unit 12 such as, for example a track ball, so that the physician is informed of the orientation with respect to the overall images G1, G2 with an orientation cube 9 mixed in the image B to which corresponding reference cubes 10, 11 are allocated in the images G1, G2. When the image B is located in the desired position, the marker M3—as shown in FIG. 6—is again mixed in by the control unit 8, i.e. a volume region VB is again defined. As can be seen from FIG. 6, the marker M3 can also include a region lying outside the displayed examination volume. After acquisition and definition of this volume region, the appertaining image dataset is also determined here by the image processor 6 and the corresponding image excerpt is clipped, see FIG. 6. Again, the corresponding, disturbing image excerpt was thus also cut out; the view onto volume parts lying therebehind is no longer impeded. The finished image B can then be stored in the memory 13.

By multiple application of the described procedure, the physician can then arbitrarily modify the image B and "tailor" it such that the physician is provided with an optimum view onto the volume region of interest to the physician. It should be noted that, instead of blanking out the defined volume region, the environment thereof alternatively can be blanked out, i.e. the volume region is presented in the following image but nots its surrounding, as the opposite of the illustrated exemplary embodiments.

Although modifications and changes may be suggested by those skilled in the art, it is the intention of the inventors to embody within the patent warranted hereon all changes and modifications as reasonably and properly come within the scope of their contribution to the art.

We claim as Our invention:

1. A method for presenting and processing an image, representing a three-dimensional volume, on a display monitor comprising the steps of:
   displaying a three-dimensional image on a display monitor, said three-dimensional image having an image orientation on said display monitor;
   changing said image orientation of said three-dimensional image on said display monitor to display a two-dimensional presentation of said three-dimensional image;
   manipulating a marker on said display monitor to select a planar contour in said two-dimensional presentation;
   defining a volume region of said three-dimensional image outlined by said contour and with a selected direction through said three-dimensional image, said three-dimensional image then consisting of the defined volume and a remainder;
   removing one of said defined volume and said remainder, as a removed image portion, from said three-dimensional image; and
   re-displaying said three-dimensional image without said removed image portion.

2. A method as claimed in claim 1 wherein the step of changing said image orientation comprises changing said image orientation of said three-dimensional image on said display monitor to display a two-dimensional presentation of said three-dimensional image in one of a plurality of parallel planes through said three-dimensional image.

3. A method as claimed in claim 2 wherein said two-dimensional presentation is a first image and wherein said marker is a first marker, and comprising the additional steps of:
   changing said image orientation of said three-dimensional image on said display monitor to display a two-dimensional presentation, perpendicular to said first image, of said three-dimensional image, as a second image;
   manipulating a second marker on said display monitor to select a planar contour in said second image; and
   defining said volume of said three-dimensional image as a volume outlined by said contour in said first image and said contour in said second image.

4. A method as claimed in claim 1 wherein at least one of said three-dimensional image and said two-dimensional presentation of said three-dimensional image is displayed on said display monitor in an image format selected from the group consisting of a projection image, a surface and a tomogram.

5. A method as claimed in claim 1 comprising mixing lines at least into said two-dimensional presentation of said three-dimensional image as said marker, and controlling movement of said lines on said display screen, to select said planar contour, using a user-operable control unit.

6. A method as claimed in claim 5 wherein said lines are freely selectable using said user-operated control unit, and wherein said lines represent a rectangle having a size which is modifiable using said user-operable control unit.

7. A method as claimed in claim 1 wherein the step of changing said image orientation comprises rotating said image orientation of said three-dimensional image on said display monitor to display said two-dimensional presentation of said three-dimensional image.

8. An apparatus for presenting and processing an image, representing a three-dimensional volume, comprising:
   an image processor in which data representing a three-dimensional volume are stored;
   a display monitor, connected to said image processor, on which said image processor displays a three-dimensional image representing said three-dimensional data, said three-dimensional image having an image orientation on said display monitor;
   means for changing said image orientation of said three-dimensional image on said display monitor to display a two-dimensional presentation of said three-dimensional image;
   said image processor generating a marker on said display monitor, and having an input unit allowing manipulation of said marker on said display monitor to select a planar contour in said two-dimensional presentation; and
   said image processor defining a volume region of the three-dimensional image outlined by said contour and with a selected direction through said three-dimensional image, said three-dimensional image then consisting of said defined volume and a remainder, and removing one of said defined volume and said remainder, as a removed image portion, from said three-dimensional image, and re-displaying said three-dimensional image on said display monitor without said removed image portion.

9. An apparatus as claimed in claim 8 wherein said means for changing said image orientation comprises means for rotating said three-dimensional image on said display screen to display said two-dimensional presentation of said three-dimensional image.

10. An apparatus as claimed in claim 9 wherein said means for changing said image orientation comprises a track ball.

11. An apparatus as claimed in claim 8 wherein said two-dimensional presentation comprises one of a plurality of parallel sections through said three-dimensional image.

12. An apparatus as claimed in claim 11 wherein said two-dimensional presentation of said three-dimensional image is a first image and wherein said marker is a first marker, and wherein said image processor changes said image orientation of said three-dimensional image on said display monitor to display a two-dimensional presentation of said three-dimensional image oriented perpendicularly to said first image, as a second image, and wherein said image processor generates a second marker on said display monitor and includes means for manipulating said second marker on said display monitor to select a planar contour in said second image, and wherein said volume region is defined by said contour in said first image and said contour in said second image.

13. An apparatus as claimed in claim 12 wherein said image processor generates a third marker on said display screen, said third marker circumscribing a further image volume, and wherein said image processor re-displays said three-dimensional image without said further image volume.

14. An apparatus as claimed in claim 8 wherein said image processor mixes lines at least into said two-dimensional presentation of said three-dimensional image on said display monitor to form said marker, and said apparatus further comprising a user-operable control unit for modifying respective positions of said lines on said display monitor.

15. An apparatus as claimed in claim 14 wherein said lines form a rectangle on said display monitor which is freely selectable by said user-operable control unit, and wherein said user-operable control unit allows changing a size of said rectangle.

16. An apparatus as claimed in claim 8 wherein said image processor comprises means for presenting at least three-dimensional image on said display screen in an image format selected from the group consisting of a projection image, a surface image and a tomogram.

17. An apparatus as claimed in claim 8 wherein said three-dimensional image which is displayed without said removed image portion comprises a processed image, and wherein said image processor includes a memory for storing said processed image.

* * * * *